United States Patent [19]
Yamasaki et al.

[11] Patent Number: 5,476,858
[45] Date of Patent: Dec. 19, 1995

[54] USE OF CARBOSTYRIL TO INCREASE SOMATOSTATIN OR FOR INHIBITING DECREASE OF SOMATOSTATIN TO TREAT DISEASES RELATED THERETO

[75] Inventors: Katsuya Yamasaki; Kazushi Sakurai, both of Tokushima, Japan

[73] Assignee: Otsuka Pharmaceutical Co., Ltd., Tokyo, Japan

[21] Appl. No.: 193,124

[22] PCT Filed: Apr. 27, 1993

[86] PCT No.: PCT/JP93/00545

§ 371 Date: Jan. 5, 1994

§ 102(e) Date: Jan. 5, 1994

[87] PCT Pub. No.: WO93/23043

PCT Pub. Date: Nov. 25, 1993

[30] Foreign Application Priority Data

May 14, 1992 [JP] Japan ..................... 4-121791

[51] Int. Cl.$^6$ .............. A61K 31/47; A61K 31/535; A61K 31/495; C07D 401/00
[52] U.S. Cl. ............. 514/312; 514/253; 544/333; 544/405; 546/157
[58] Field of Search ............... 514/233, 236, 514/253, 312; 544/333, 405; 546/157

[56] References Cited

U.S. PATENT DOCUMENTS

| 4,578,381 | 3/1986 | Uchida et al. | 514/233 |
| 4,612,302 | 9/1986 | Szabo et al. | 514/11 |

FOREIGN PATENT DOCUMENTS

| 374329 | 3/1991 | Japan . |
| 3145468 | 6/1991 | Japan . |
| 5148143 | 6/1993 | Japan . |

OTHER PUBLICATIONS

Folia Pharmacol. Jpn. vol. 97, No. 6, 1991, pp. 371–380 S. Kawano et al. 'Protective Effect Of Rebamipide (OPC–12759) On The Gastric Mucosa In Rats And Humans' see p. 377; table 3.
'Dorland's Illustrated Medical Dictionary, 26th Edition' 1985, W. B. Saunders Company, Philadelphia see p. 1222.
De,A,3 324 034 (Otsuka Pharmaceutical Co., Ltd.) Jan. 5, 1984 see pp. 24–25.

Primary Examiner—T. J. Criares
Attorney, Agent, or Firm—Sughrue, Mion, Zinn, Macpeak & Seas

[57] ABSTRACT

An agent for increasing secretion of somatostatin or inhibiting decrease of secretion of somatostatin which comprises as an active ingredient a carbostyril compound of the formula:

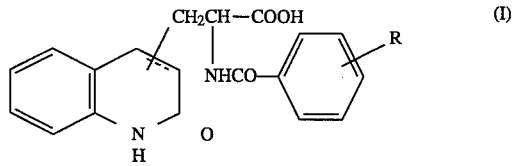

or a salt thereof, which is useful for treating diseases associated with the decrease of somatostatin such as esophagitis, Alzheimer's disease, etc.

2 Claims, No Drawings

USE OF CARBOSTYRIL TO INCREASE SOMATOSTATIN OR FOR INHIBITING DECREASE OF SOMATOSTATIN TO TREAT DISEASES RELATED THERETO

This application is a continuation of PCT/JP93/00545 filed Apr. 27, 1993.

TECHNICAL FIELD

This invention relates to an agent for increasing secretion of somatostatin or for inhibiting decrease of secretion of somatostatin in the bio-body. More particularly, it relates to a pharmaceutical composition useful for increasing secretion of somatostatin or for inhibiting decrease of section of somatostatin which comprises as an esstial active ingredient a carbostyril compound of the formula:

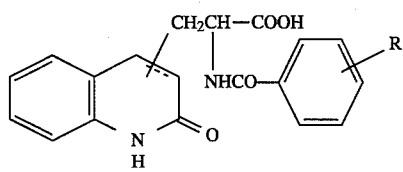

wherein R is a halogen atom, and the propionic acid substituent is substituted at 3- or 4-position on the carbostyril nucleus, and the bond between 3- and 4-positions is single or double bond, or a pharmaceutically acceptable salt thereof, preferably 2-(4-chlorobenzoylamino)-3-(2-quinolon-4-yl)propionic acid or a pharmaceutically acceptable salt thereof.

PRIOR ART

It is known that somatostatin is a growth hormone-release inhibiting factor secreted in the bio-body and when the secretion of somatostatin is decreased, there are induced various diseases, such as esophagitis, Zollinger-Ellison syndrome, diarrhea, erethistic colitis, various cancers, hepatitis, portal hypertension, headache, migraine, Alzheimer's disease, presbyophrenia, pancreatitis, acromegalia.

The present inventors have intensively studied to find a new drug useful for treating the diseases associated with the decrease of somatostatin, and have found that the carbostyril compounds of the above formula (1), particularly 2-(4-chlorobenzoylamino)-3-(2-quinolon-4-yl)propionic acid or a pharmaceutically acceptable salt thereof, are useful as an agent for increasing secretion of somatostatin or for inhibing decrease of secretion of somatostatin.

The carbostyril compounds of the formula (I) and processes for the preparation thereof are disclosed in Japanese Patent Second Publication (Kokoku) No. 35623/1988, wherein it is disclosed that the carbostyril compounds are useful as an anti-ulcer drug.

SUMMARY OF THE INVENTION

This invention provides an agent for increasing secretion of somatostatin or inhibiting decrease of secretion of somatostatin comprising as an essential active ingredient a carbostyril compound of the formula (I) or a pharmaceutically acceptable salt thereof, a method of the treatment of diseases associated with decrease of somatostatin by administering the agent as set forth above, and use of the agent for the treatment of diseases associated with decrease of somatostatin.

DETAILED DESCRIPTION OF THE INVENTION

The agent of this invention is usually in the form of conventional pharmaceutical preparations, for example, preparations suitable for oral administration such as tablets, pills, powders, granules, capsules, solutions, suspensions, emulsions, and preparations for parenteral administration such as suppositories and injections (e.g. solutions, suspensions, etc.). These preparations can be prepared by a conventional method with conventional pharmaceutically acceptable carriers or diluents, such as fillers, thickening agents, binders, wetting agents, disintegrators, surfactants, lubricants, and the like.

In order to form in tablets, there are used conventional pharmaceutically acceptable carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (starches, lactose, kaolin, bentonite, collidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets.

In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like.

In the preparation of suppositories, the carriers include, for example, polyethylene glycol, cacao butter, higher alcohols, higher alcohol esters, gelatin, semi-synthetic glycerides, and the like.

Capsules can be prepared by charging a mixture of the compound of this invention with the above carriers into hard gelatin capsules or soft capsules in a usual manner.

In the preparation of injections, the solutions, emulsions or suspensions are sterilized and are preferably made isotonic with the blood. In the preparation of these solutions, emulsions and suspensions, there are used conventional diluents, such as water, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The agent for increasing secretion of somatostatin or inhibiting decrease of secretion of somatostatin of this invention is useful for the treatment of diseases associated with the decrease of somatostatin, such as esophagitis, Zollinger-Ellison syndrome, diarrhea, erethistic colitis, various cancers, hepatitis, portal hypertension, headache, migraine, Alzheimer's disease, presbyophrenia, pancreatitis, acromegalia.

The amount of the active component carbostyril compound of this invention to be incorporated into the preparations is not specified but may be selected from a broad range, but it is usually in the range of from 1 to 70% by weight, preferably in the range of 5 to 50% by weight.

The somatostatin-increasing or decrease-inhibiting agent of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if required, suppositories are administered in intrarectal route.

The dosage of the agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in the pharmaceutical preparations in an amount of 10 to 1000 mg per the dosage unit.

EXAMPLES

The somatostatin-increasing or decrease-inhibiting agent of this invention is illustrated by the following Preparations and Pharmacological experiments.

Preparation 1

Film coated tablets are prepared from the following components.

| Components | Amount |
| --- | --- |
| 2-(4-Chlorobenzoylamino)-3-(2-quinolon-4-yl)-propionic acid | 150 g |
| Abicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 2-(4-Chlorobenzoylamino)-3-(2-quinolon-4-yl)-propionic acid | 150 g |
| Citric acid | 1.0 g |
| Lactose | 33.5 g |
| Dicalcium phosphate | 70.0 g |
| Pluronic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium laurylsulfate | 3.0 g |
| Dry magnesium stearate | 3.0 g |
| Ethanol | q.s. |

The active compound of this invention, citric acid, lactose, dicalcium phosphate, Pluronic F-68 and sodium laurylsulfate are mixed. The mixture is screened with No. 60 screen and is granulated in wet with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixtue is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
| --- | --- |
| 2-(4-Chlorobenzoylamino)-3-(2-quinolon-4-yl)-propionic acid | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan mono-oleate are dissolved in the above solution. To the solution is added distilled water for injection to adjust to the desired volume, and the solution is sterilized by filtering with an appropriate filter paper to give an injection preparation.

Pharmacological Test 1

Male Wistar rats were freely haven take 5 mM sodium taurocholate with drinking water. After 6 months, the administration of sodium taurocholate was stopped and then the active compound of this invention 2-(4-chlorobenzoylamino)-3-(2-quinolon- 4-yl)propionic acid (hereinafter referred to "Compound A") was orally administered in doses of 6 mg/kg/day or 60 mg/kg/day together with a feed. After Compound A was administered for 4 weeks, the rats were killed and the stomach was removed. The mucosal membrane of stomach was collected by scraping, and the content of somatostatin in the gastric mucosa was measured by radioimmunoassay. In the reference group, the above was repeated except that Compound A was not administered and the content of somatostatin in the gastric mucosa was measured likewise, and further in the normal control group to which no sodium taurocholate was administered, the content of somatostatin was measured likewise.

The results are shown in the following Table 1.

TABLE 1

| Treated groups | Dose (mg/kg/day) | Content of somatostatin (ng/g) |
| --- | --- | --- |
| Normal group | — | 45.4 |
| Reference group | — | 19.1 |
| Compound A-administered group | 6 | 28.1 |
|  | 60 | 40.7 |

As is clear from the above results, Compound A of this invention inhibited dose-dependently the decrease of somatostatin content.

Pharmacological Test 2

Normal rats were fed with a solid feed mixed with Compound A for four weeks, whereby Compound A was administered in an amount of 6 mg/kg/day, 60 mg/kg/day or 100 mg/kg/day. After Compound A was administered, the mucosal membrane of stomach was collected like in the above test 1. The brain was also removed. The content of somatostatin in the gastric mucosa and in the brain was measured likewise. In the control group to which no Compound A was administered, the content of somatostatin was measured likewise.

The results are shown in the following Table 2.

TABLE 2

| Treated groups | Dose (mg/kg/day) | Content of somatostatin in gastric mucosa (ng/g of tissue weight in wet) | Content of somatostatin in the brain (ng/g of tissue weight in wet) |
| --- | --- | --- | --- |
| Control group | — | 274 ± 60 (9)* | 54 ± 4 (9)* |
| Compound A-administered group | 6 | 471 ± 79 (10) | 101 ± 13 (10) |
|  | 60 | 595 ± 88 (10) | 98 ± 13 (10) |
|  | 100 | 714 ± 81 (10) | 128 ± 11 (9) |

*The number within the parenthesis means number of animals.

It is clear from the above results that the administration of Compound A of this invention in an amount of 6, 60 and 100 mg/kg/weight increased the content of somatostatin in the gastric mucosa in the ratio of 72, 117, 161% respectively in comparison with the content in the control group: 274±60 ng/g of tissue weight in wet, and also increased the content in the brain in the ratio of 87, 81 and 137% respectively in comparison with the content in the control group: 54±4 ng/g of tissue weight in wet.

We claim:

1. A method for treating a subject afflicted with a disease associated with a decrease of somatostatin selected from the group consisting of esophagistis, Zollinger-Ellison syndrome, diarrhea, erethistic colitis, hepatitis, portal hypertension, headache, migraine, Alzheimer's disease, presbyophrenia, pancreatitis and acromegalia, which comprises administering an effective amount of a carbostyril compound of the following formula which increases the secretion of somatostatin or inhibits the decrease of secretion of somatostatin:

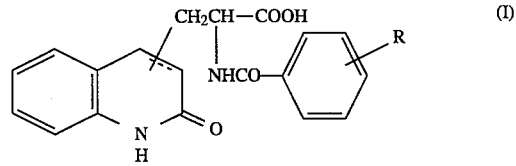

wherein R is a halogen atom, and the propionic acid substituent is substituted at the 3- or 4-position on the carbostyril nucleus, and the bond between the 3- and 4-positions is a single or double bond, or a pharmaceutical acceptable salt thereof.

2. The method according to claim 1, wherein the carbostyril compound is 2-(4-chlorobenzoylamino)-3-(2-quinolon- 4-yl)propionic acid or a pharmaceutically acceptable salt thereof.

* * * * *